United States Patent [19]
Ovadia-Blechman et al.

[11] Patent Number: 6,129,674
[45] Date of Patent: Oct. 10, 2000

[54] METHOD FOR DETERMINING THE DEGREE OF OCCULSION AND ELASTICITY IN BLOOD VESSELS AND OTHER CONDUITS

[75] Inventors: Zehava Ovadia-Blechman, Ramat-Gam; Shmuel Einav, Herzliya; Michael Eldar, Raman-Hasharon, all of Israel

[73] Assignee: Ramot of Tel-Aviv University, Tel-Aviv, Islamic Rep. of Iran

[21] Appl. No.: 09/276,877

[22] Filed: Mar. 26, 1999

[51] Int. Cl.$^7$ .......................................................... A61B 5/02
[52] U.S. Cl. ................................................. 600/481; 73/37
[58] Field of Search ..................................... 600/481, 485, 600/486, 479, 480, 465, 468, 454; 73/37

[56] References Cited

U.S. PATENT DOCUMENTS

| | | | |
|---|---|---|---|
| 4,109,642 | 2/1999 | Reid et al. | 600/457 |
| 4,572,199 | 2/1986 | LaCourse | 600/434 |
| 4,692,864 | 9/1987 | Shimoni et al. | 364/414 |
| 5,241,963 | 9/1993 | Shankar | 600/481 |
| 5,297,556 | 3/1994 | Shankar | 600/481 |
| 5,343,867 | 9/1994 | Shankar | 600/481 |
| 5,752,522 | 5/1998 | Murphy . | |
| 5,872,861 | 2/1999 | Makram-Ebeid | 382/130 |

OTHER PUBLICATIONS

Pijls et al., New England Journal of Medicine; 334:1703–1708, 1996.

*Primary Examiner*—Cary O'Connor
*Assistant Examiner*—Navin Natnithithadha
*Attorney, Agent, or Firm*—Baker & Botts L.L.P.

[57] ABSTRACT

The invention provides a method for determining the degree of partial occlusion of a conduit, comprising the steps of:
a) producing a graphical plot of fluid pressure versus fluid flow rate through said conduit;
b) determining the value of one or more of the following variables:
   (iv) the PFLA variable consisting of the area enclosed by said graphical plot;
   (v) the slope of the line joining the two inflection points situated at the extremities of the major axis of said graphical plot;
   (vi) the y-axis intercept of the line joining the two inflection points situated at the extremities of the major axis of said graphical plot;
c) determining the degree of partial occlusion of said conduit by comparing one or more of the above variables, with an appropriate calibration curve, said calibration curve comprising values of the chosen variable for a conduit of the same type as the tested conduit, at predetermined known degrees of occlusion.

The invention also provides a method for determining the elastic properties of conduits, and apparatus for determining both the degree of partial occlusion and the elastic properties of said conduits.

15 Claims, 13 Drawing Sheets

METHOD FOR DETERMINING THE DEGREE OF OCCULSION AND ELASTICITY IN BLOOD VESSELS AND OTHER CONDUITS

FIELD OF THE INVENTION

The present invention is concerned with a method for determining the degree of constriction of blood vessels, grafted blood-vessel replacements and other types of conduit. The method further permits the quantitative assessment of the elastic properties of the aforementioned conduits.

BACKGROUND OF THE INVENTION

The occlusion (stenosis) of small blood vessels that occurs, for example, as a result of the accumulation of atherosclerotic plaques, is a major cause of morbidity and mortality in the western world. While the detection of such occlusions may be readily performed by several techniques including angiography and ultrasonic echocardiography, the accurate measurement of both the degree of vascular stenosis and hence of vascular dysfunction, without resorting to highly invasive techniques, is much more difficult to achieve.

A number of techniques for quantifying vascular occlusion are known in the art. While some of these methods provide reliable quantitative data, they are generally highly invasive in nature. Examples of such methods include the technique described in U.S. Pat. No. 5,752,522 (Murphy), in which the cross-sectional dimensions of a blood vessel are determined by inflation of a balloon catheter within the blood vessel lumen, until the balloon diameter matches the lumen diameter. A further method is the measurement of myocardial fractional flow reserve, in which an index representing the degree of coronary artery stenosis is calculated from measurements of mean distal intracoronary pressure and of mean arterial pressure (Pijls et al. New Engl. J. Med. 334: 1703–1708, 1996).

Both of the abovementioned prior art methods for measuring the degree of vascular stenosis are technically demanding in that they require catheters to be positioned at very specific locations in relation to the site of the stenosis, as well as the use of vasodilatory drugs.

It has now been surprisingly found, and this is an object of the invention, that it is possible to obtain an accurate measure of the degree of constriction or occlusion of a conduit from simultaneous measurement of fluid pressure and flow through said conduit, over a period of time. Furthermore, these simultaneous measurements may be used to determine the elastic properties of conduits. Such determinations are of clinical importance, as they permit assessment of the extent of, for example, atherosclerotic disease in blood vessels. In this system, the relationship between pressure and flow is not a simple linear one. Rather, when plotted graphically, the resulting curve is in the form of a closed loop, whose area may be measured and used to determine the degree of occlusion of the conduit. Furthermore, the slope and y-axis intercept of the line joining the two inflection points situated at the extremities of the major axis of the loop, may also be used to determine the same variable, that is, the degree of occlusion of the conduit, as well as its elasticity.

It has further been unexpectedly found that a quantitative measure of the elastic properties of a conduit may be derived from the polynomial equation that describes the relationship between the above-described area enclosed by the pressure-flow relationship and the degree of occlusion of a conduit of the same material.

It is a purpose of this invention to provide a method for the accurate quantification of the degree of partial constriction of blood vessels and other types of tube or conduit.

It is another purpose of this invention to provide a method for accurately quantifying the degree of partial constriction that uses fluid pressure and flow data obtained by minimally invasive methods.

It is yet another purpose of this invention to provide such a method that calculates the degree of partial constriction in a manner that is independent of the apparatus or technique used to obtain the pressure and flow data.

It is a further purpose of this invention to provide a method for calculating the degree of partial occlusion of a conduit that is independent of the distance between the site of said partial occlusion and the site of the pressure and flow measurements, and without the requirement for vasodilatory or other drugs.

It is a further purpose of this invention to provide apparatus for determining the degree of partial occlusion of a conduit.

It is a further purpose of this invention to provide a method for assessing the elastic properties of a conduit, using fluid pressure and flow rate data.

It is a further purpose of this invention to provide apparatus for determining the elastic properties of a conduit.

Other objects and advantages of the invention will become apparent as the description proceeds.

SUMMARY OF THE INVENTION

The invention is primarily directed to a method for determining the degree of partial occlusion of a conduit, comprising the following steps:

a) producing a graphical plot of fluid pressure versus fluid flow rate through said conduit;

b) determining the value of one or more of the following variables:
   (i) the PFLA (pressure flow loop area) variable consisting of the area enclosed by said graphical plot;
   (ii) the slope of the line joining the two inflection points situated at the extremities of the major axis of said graphical plot;
   (iii) the y-axis intercept of the line joining the two inflection points situated at the extremities of the major axis of said graphical plot.

c) determining the degree of partial occlusion of said conduit by comparing one or more of the above variables, with an appropriate calibration curve.

The term "appropriate calibration curve" refers to a graphical plot of the PFLA variable, slope or y-axis intercept values, obtained from in vitro measurements made in conduits constructed of the same material, whose degree of partial occlusion is determined by independent means. This term also refers to the use of the mathematical equation that describes said calibration curve.

The aforementioned variables (PFLA, slope and y-axis intercept) are graphically depicted in FIG. 1, wherein PFLA is represented by S, the y-axis intercept by b, and the slope of the curve (d) being represented by $\alpha$.

In one aspect of the invention, the method of measuring partial constriction is applied to blood vessels that have become constricted, or are suspected of being constricted, as a result of atherosclerosis or any other pathological, physiological or physical cause.

In another aspect, the invention provides a method for measuring the degree of partial constriction in a synthetic blood vessel replacement, such as is used for surgical graft procedures.

The invention also provides for a method for determining the degree of partial occlusion of a blood vessel or synthetic blood vessel graft, wherein the fluid pressure and flow rate are measured by inserting one or more suitable probes through a catheter introduced into the blood vessel or graft.

The invention further provides a method for determining the degree of partial occlusion of a blood vessel or synthetic blood vessel graft, wherein flow rate and/or fluid pressure are determined by the use of measuring devices situated external to the wall of the conduit.

The invention further provides a method for determining the degree of partial occlusion of a blood vessel or synthetic blood vessel graft, wherein flow rate and/or fluid pressure in the conduit are measured by the use of measuring devices situated remote from said conduit.

The invention also provides for the determination of the elastic properties of a conduit, comprising the steps of:
a) producing a graphical plot of fluid pressure versus fluid flow rate through said conduit;
b) determining the value of one or more of the following variables:
   (i) the PFLA (pressure flow loop area) variable consisting of the area enclosed by said graphical plot;
   (ii) the slope of the line joining the two inflection points situated at the extremities of the major axis of said graphical plot;
   (iii) the y-axis intercept of the line joining the two inflection points situated at the extremities of the major axis of said graphical plot.
c) producing a graphical plot of the PFLA variable, as defined in (b), versus predetermined known degrees of occlusion, and deriving the polynomial equation of the plot thereby obtained, in the form of $y=AX^2+BX+C$;
d) determining the degree of radial compliance of said conduit by separately comparing one or both of the coefficients A, B and C of the aforementioned polynomial equation with an appropriate calibration curve, said calibration curve comprising a plot of values of the chosen coefficient, A, B or C, versus predetermined known levels of radial compliance; and optionally:
   (1) comparing the abovementioned slope obtained with the tested conduit with the slope obtained with one or more standard conduits, to determine the relative elastic properties thereof; and/or
   (2) comparing the abovementioned y-axis intercept obtained with the tested conduit with the y-axis intercept obtained with one or more standard conduits, to determine the relative elastic properties thereof.

It is to be emphasized that the above-mentioned polynomial equation is derived from a series of pressure and flow measurements of the conduit under study, and that this polynomial equation provides a means of characterizing the elastic properties of said conduit.

In one preferred embodiment, the determination of elastic properties is made in a blood vessel. In another preferred embodiment, this determination is made in a synthetic blood vessel replacement, such as is used in clinical graft procedures.

The above method of measuring the elasticity of blood vessels or their synthetic replacements may be used when the fluid pressure and flow rates are measured by inserting suitable probe(s) through a catheter introduced into the lumen of said conduits.

Alternatively, the method for measuring elastic properties may also be used when flow rate and/or fluid pressure are measured by the use of measuring devices situated external to the wall of the conduit.

The invention further provides a method for measuring the elastic properties of a blood vessel or synthetic blood vessel graft, wherein flow rate and/or fluid pressure in the conduit are measured by the use of measuring devices situated remote from said conduit.

The invention further provides for apparatus for use in determining the degree of partial occlusion and/or elastic properties of a conduit, comprising:
a) fluid pressure and flow rate measuring devices;
b) data receiving apparatus to receive and record data generated by said measuring devices;
c) data processing apparatus to process the data generated by said measuring devices, to determine the values of the PFLA variable and the slope and y-axis intercept variables, as defined above, and to determine the degree of partial occlusion and elastic properties therefrom;
d) algorithms, associated with said apparatus, for performing the data analysis tasks described above.

This apparatus may further comprise a visual display unit, and/or apparatus for producing a printed output.

All the above and other characteristics and advantages of the invention will be further understood from the following illustrative and non-limitative examples of preferred embodiments thereof.

BRIEF DESCRIPTION OF THE DRAWINGS

The present invention will be more clearly understood from the detailed description of the preferred embodiments and from the attached drawings in which.

DETAILED DESCRIPTION OF PREFERRED EMBODIMENTS

Without wishing to be restricted to any specific theory, it is believed that the non-linear relationship between pressure and flow in the systems studied and described herein, is a consequence of the elastic nature of the walls of most commonly found conduits (e.g. blood vessels, elastic, latex and rubber tubes). According to this theory, the elastic expansion and recoil of the conduit walls causes perturbation of the pressure-flow relationship, and the resulting graphical plot of such a relationship is in the form of a hysteresis loop. In the method of the invention, the relationship between fluid pressure and flow is plotted graphically, and the area surrounded by the closed loop is measured. This area has the units [$V^2$], and is termed the PFLA variable. It has been surprisingly found that the PFLA variable is a function of the degree of constriction or occlusion of the conduit. For all materials studied thus far, the relationship between PFLA and the degree of occlusion is a robust one, and may be described by a single polynomial equation, said equation being derived by non-linear regression. The method of the present invention thus provides for the measurement of the degree of occlusion of conduits in absolute terms, the quantitative degree of occlusion being derived either by interpolation from a calibration curve constructed from loop area—percentage occlusion relationships obtained from a conduit constructed of the same physical (or biological) material, or by application of the polynomial equation describing said calibration curve. An important feature of this method is that the result obtained for the degree of occlusion is independent of the distance between the site of the occlusion and the location of the pressure and flow measuring devices, and does not require the use of vasodilatory drugs. This feature simplifies the procedures of flow and pressure measurement, and also contributes to the precision of the results obtained by application of this method. This lack of dependence on distance from the occlusion site also confers great flexibility on the method described herein, as said method is thereby independent of the techniques used for measuring fluid pressure and flow through the conduit under study, whether this be a natural blood vessel, synthetic blood vessel replacement for use in surgical graft procedures, or any other type of pipe, tubing or conduit.

It has similarly found that the slope and y-axis intercept of the line joining the two inflection points situated at the extremities of the major axis of the loop-shaped graph defining the pressure-flow rate relationship of a conduit, are also (when taken independently) functions of the degree of occlusion of said conduit. All of the above-described advantages of the method for determining partial occlusion of a conduit using the PFLA variable equally apply to the use of the slope and y-intercept to determine said partial occlusion.

Figure 1:
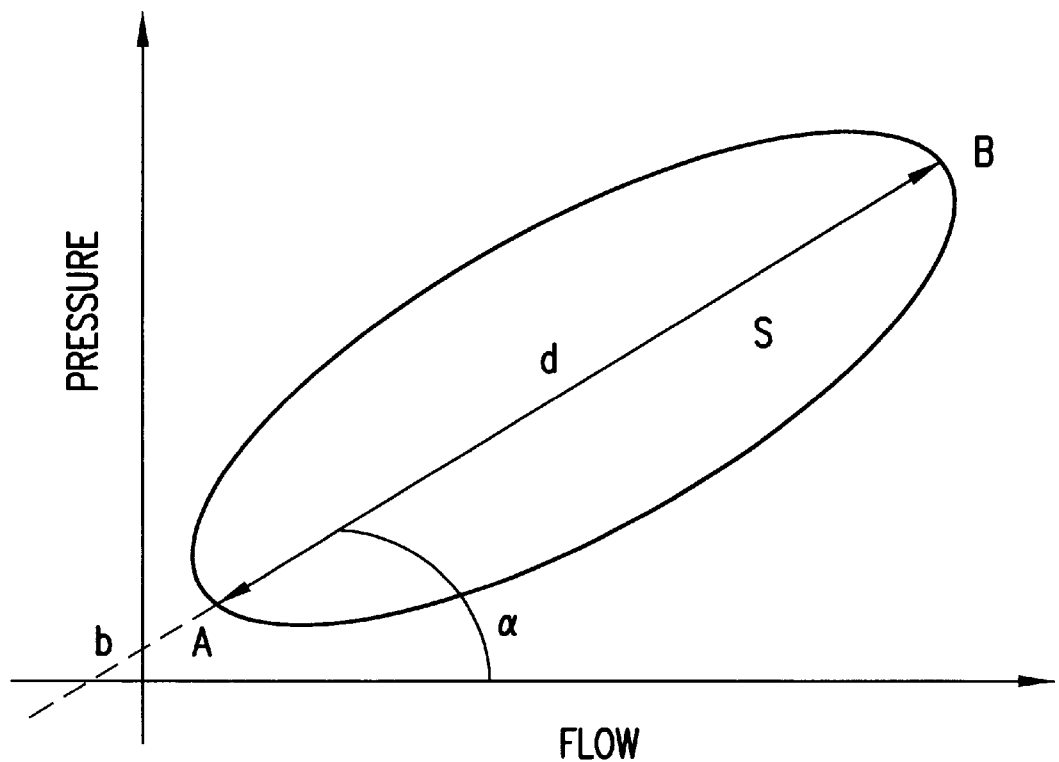
FIG. 1 is a schematic diagram of the pressure-flow relationship depicting the variables measured therefrom.

It has also been surprisingly found that a quantitative measure of the elastic properties of a conduit of a given material or type may be derived from the non-linear fluid pressure-fluid flow rate relationship described above. Examination of the pressure-flow rate graphs given in the examples below (e.g. FIGS. 4, 5 and 6) will serve to illustrate the use of these data in determining the elastic properties of a conduit. It has already been discussed above, and will be seen from the aforementioned figures, that the area enclosed by the pressure-flow rate curve is a function of the degree of occlusion of the conduit. Comparison between FIG. 5, on the one hand, and FIGS. 4 and 6 on the other hand, however, indicates that the quantitative relationship between curve area and degree of occlusion is different for different conduit materials. It may further be seen by comparison of FIG. 5 with FIGS. 4 and 6 that both the slope of the line corresponding to the major axis of the essentially ellipsoid pressure-flow curve ($\alpha$, in FIG. 1), and the y-axis intercept of that line (b, in FIG. 1), also show differences in their relationship with degree of occlusion, according to the material of which the conduit is made. The polynomial equations describing the relationship between the degree of conduit occlusion and the area of the pressure-flow curve, which were described hereinabove, are of the form:

$$y = Ax^2 + Bx + C.$$

It has been surprisingly found that there is a high degree of correlation between the coefficients A, B and C of these equations (taken independently) and the radial compliance of the conduit under study. The radial compliance of a tube is defined by the following relationship:

$$\text{Radial compliance } (Cr) = (dD/D_0)/dP;$$

where $dD/D_0$ is the change in diameter of the conduit, and dP is the corresponding change in fluid pressure within the lumen of said conduit. Thus, by producing calibration curves relating the values of the coefficients A, B or C (taken independently) for a conduit of given material to compliance determined experimentally for conduits of the same material, it is possible to derive either the compliance, or Young's Modulus (the inverse of compliance) for said conduit. In addition, the differing values of the slope and y-axis intercept variables (as defined hereinabove) seen in conduits constructed of different materials—for example rubber (FIG. 5) compared with either latex (FIG. 4) or clinical graft material (FIG. 6) indicate that said variables may also be used to determine the elastic properties of conduits.

The method of the present invention is applicable to all types of pipes and tubing including: water pipes, sewage pipes, conduits for electrical cables, gas pipes, blood vessels, and synthetic replacements for blood vessels for use in graft procedures. However, due to the special interest in measuring partial occlusion in blood vessels and grafts, the following illustrative examples will relate only to these types of sample. It is to be understood, however, that the scope of the invention is in no way limited to the conduit types described in this example, but rather is inclusive of all other types of tubing, pipe or conduit.

EXAMPLE 1

In vitro Determination of Degree of Constriction

The in vitro method described hereinbelow was used to determine the degree of luminal constriction of the following samples:

a) latex tube 30 cm in length, 3.45 mm external diameter (Ro) and 2.75 mm internal diameter (Ri).

b) rubber tube 125 cm length, 3.35 mm Ro and 2.15 mm Ri.
c) clinically-used graft (Hybrid PTFE™ Vascular Grafts, Atrium, N.H., USA) 40 cm length, 3.7 mm Ro and 3 mm Ri.

Method

Figure 2:
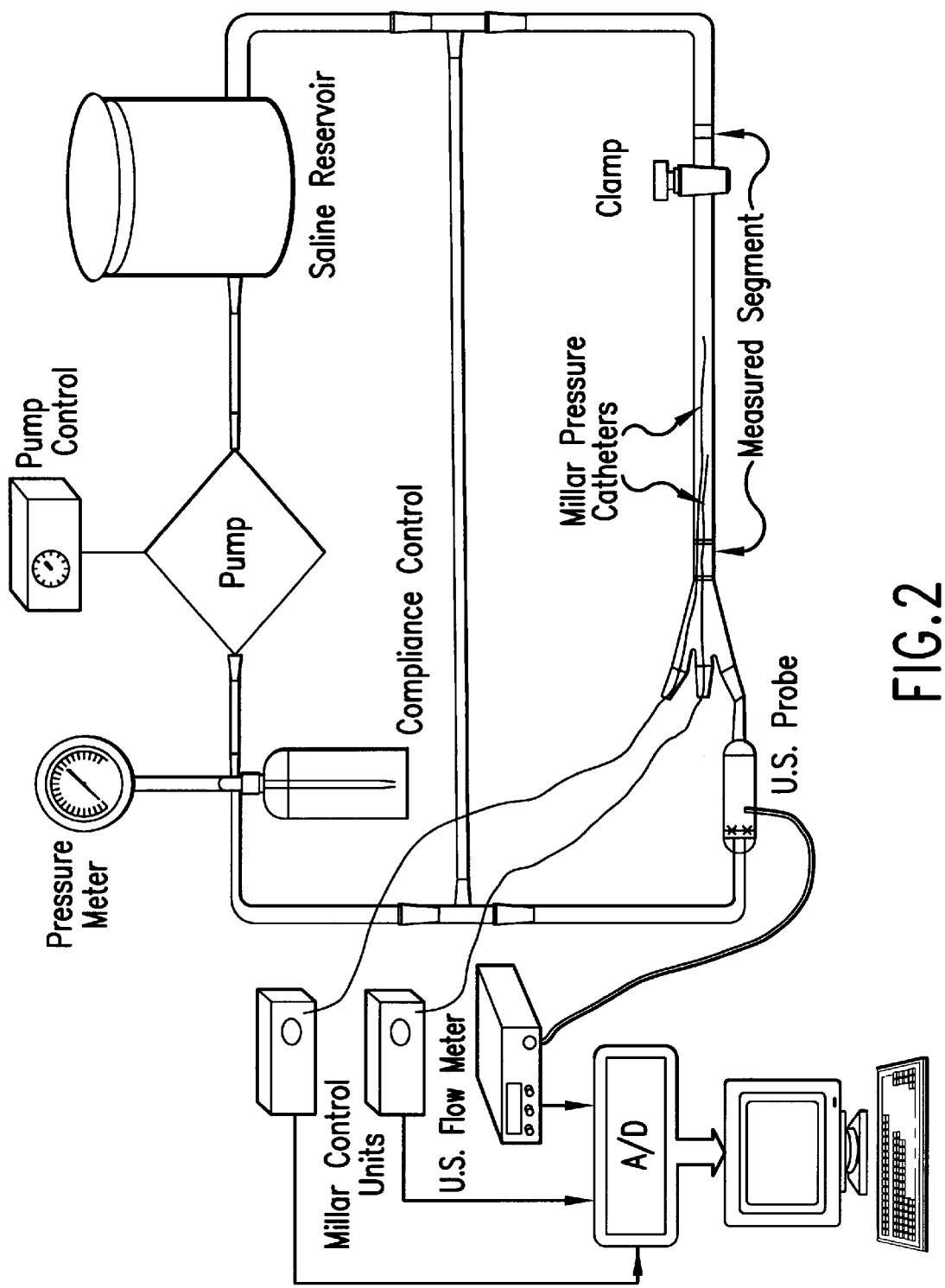
FIG. 2 is a schematic representation of the measurement and analysis system used in the in vitro determinations of the degree of partial occlusion in small-diameter conduits.
Figure 3A:
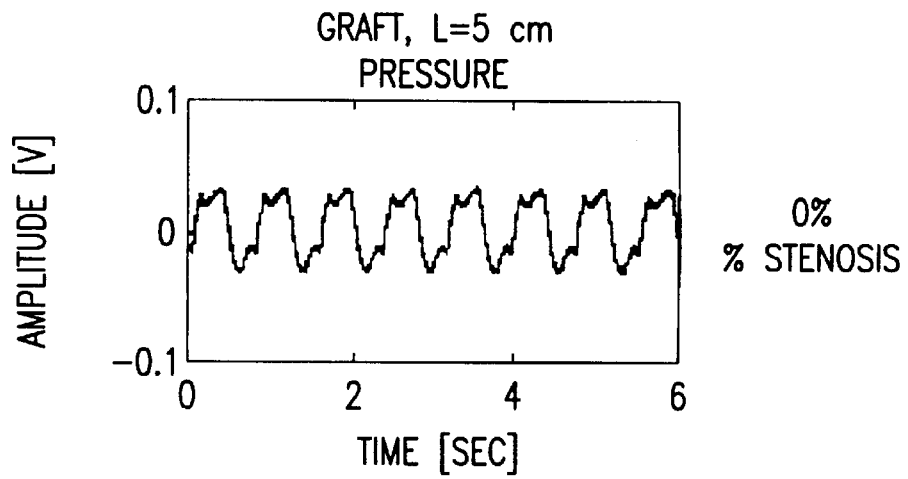
FIG. 3 depicts the fluid pressure and fluid flow waves measured in a sample of clinically-used graft material, as measured at 0, 25 and 50% degrees of constriction.
Figure 3B:
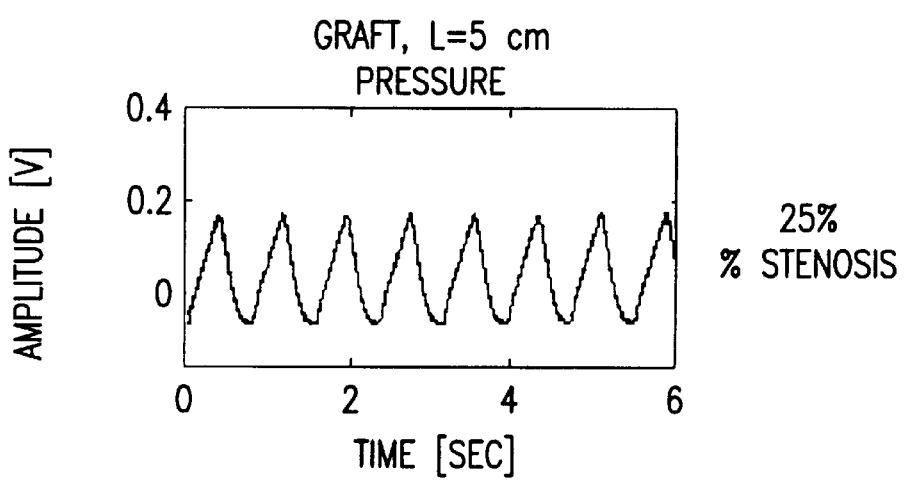
Figure 3C:
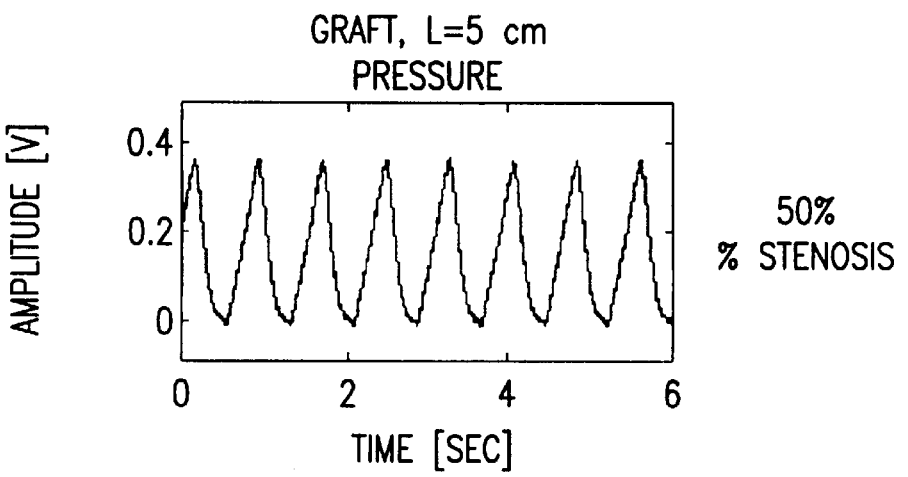
Figure 3D:
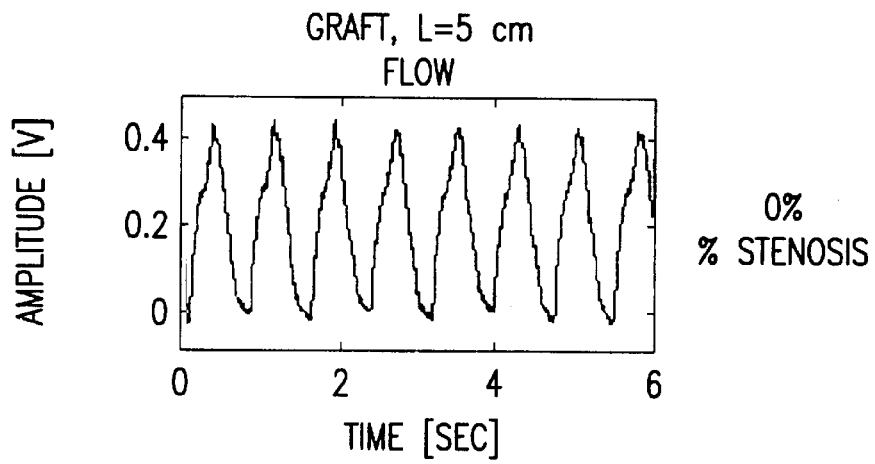
Figure 3E:
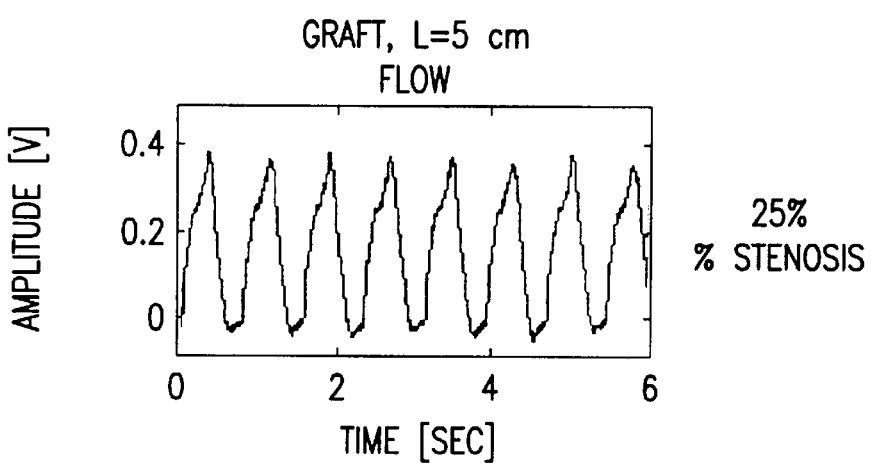
Figure 3F:
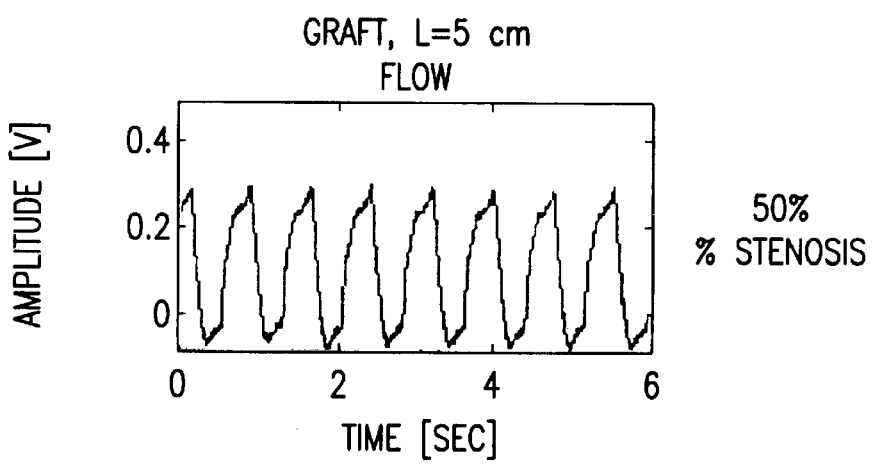
Figure 4A:
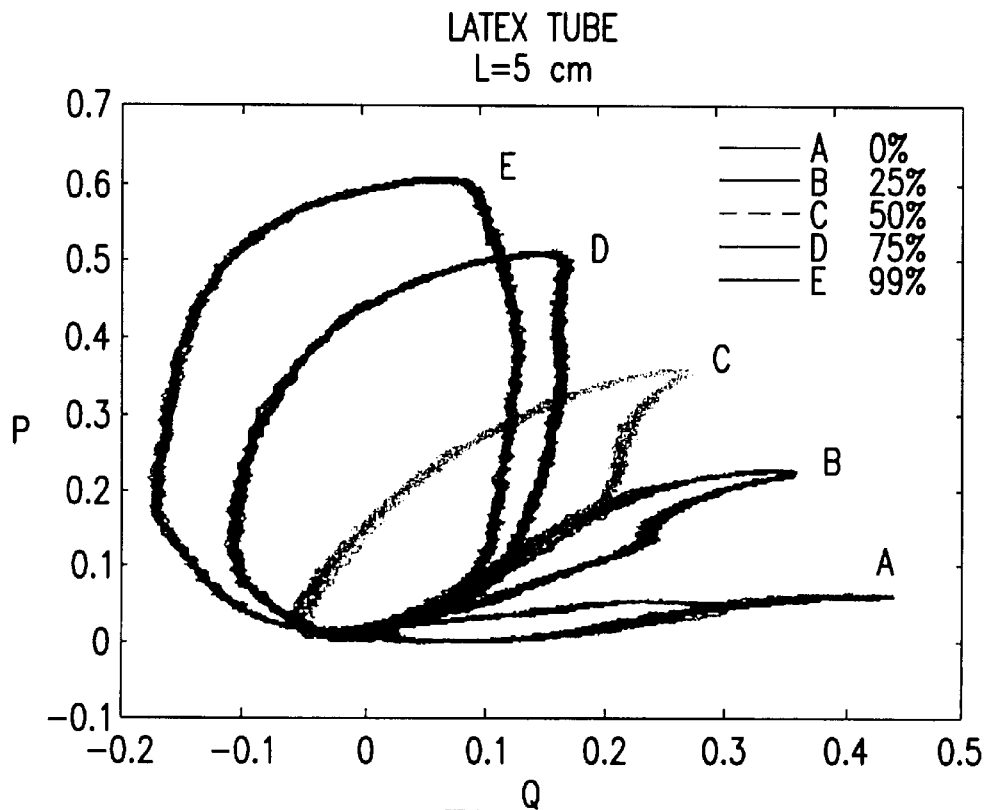
FIG. 4 is a graphical depiction of the fluid pressure-fluid flow relationship derived from in vitro measurements made in latex tubes of length 30 cm, and having external and internal diameters of 3.45 mm and 2.75 mm respectively. Fluid pressure and flow are indicated by P and Q, respectively, and are each measured in units of voltage.
Figure 4B:
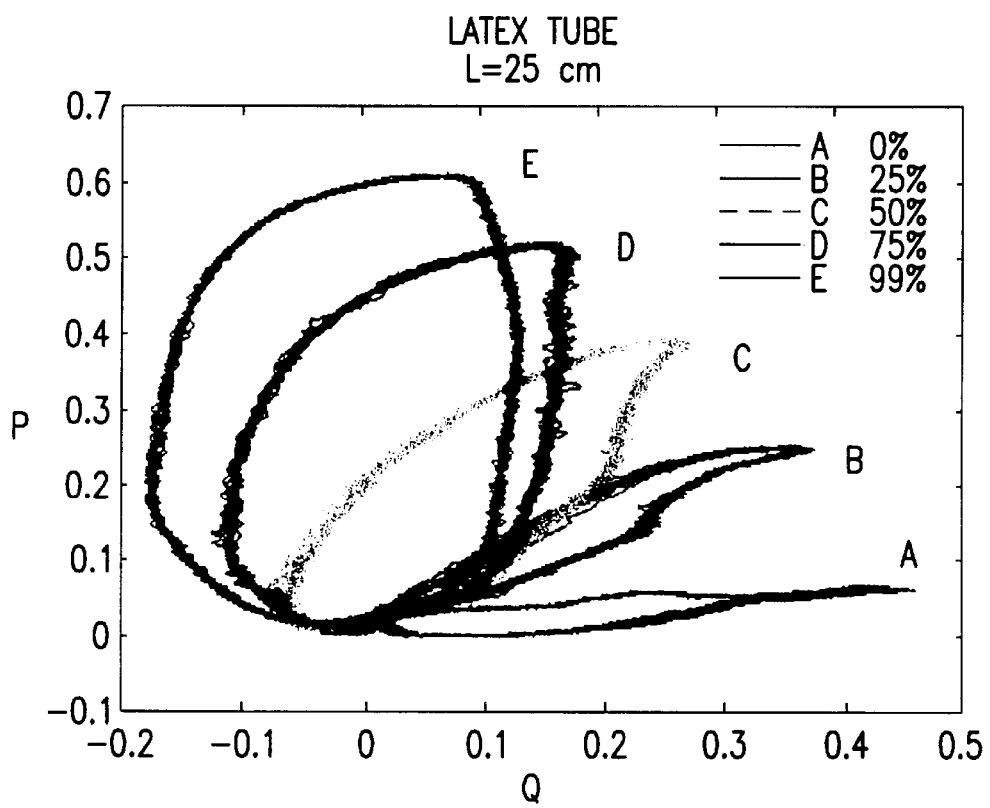
Figure 4C:
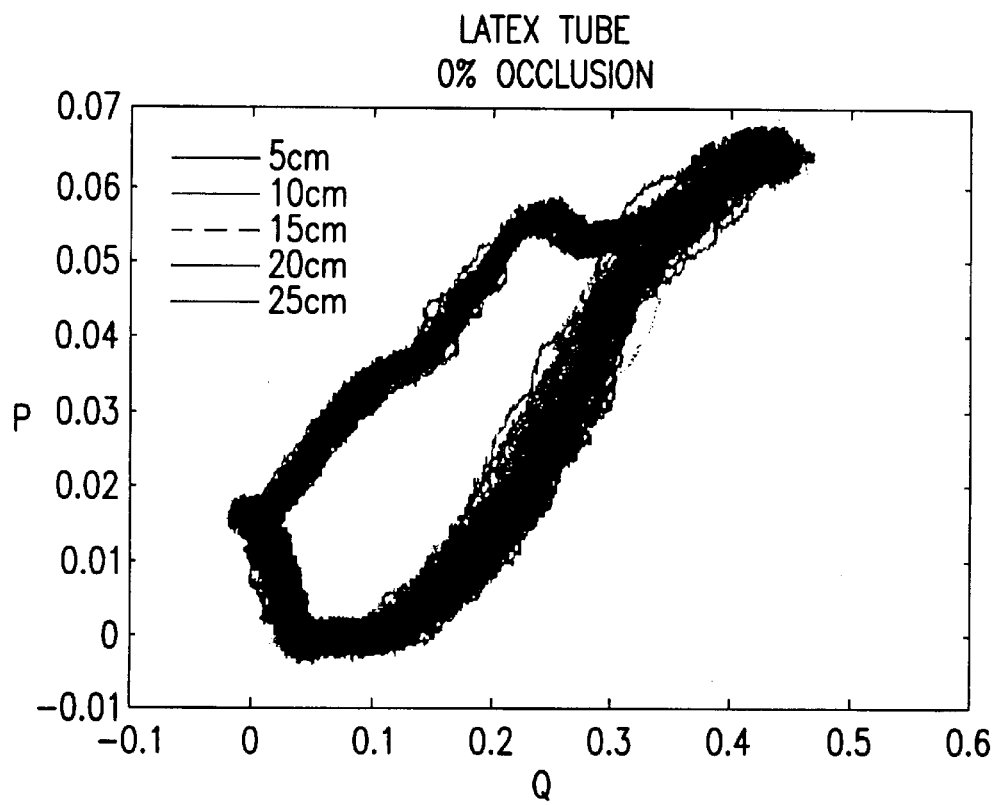
Figure 4D:
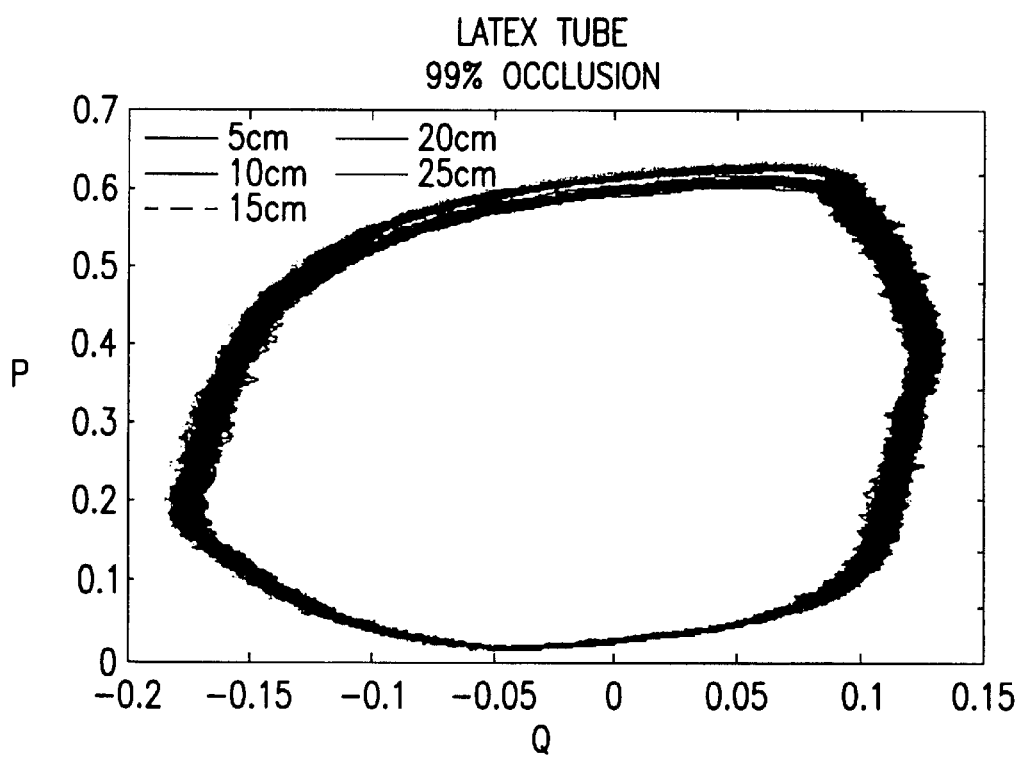
Figure 5A:
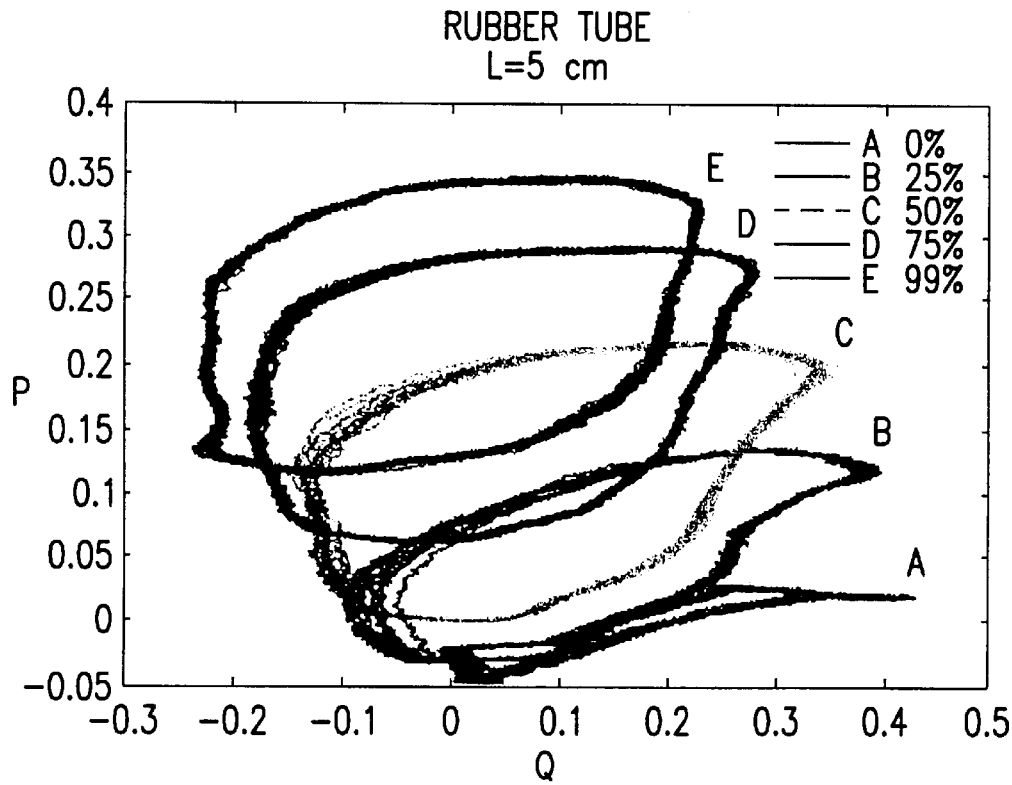
FIG. 5 is a graphical depiction of the fluid pressure-fluid flow relationship derived from in vitro measurements made in rubber tubes of length 125 cm, and having external and internal diameters of 3.35 mm and 2.15 mm respectively. Fluid pressure and flow are indicated by P and Q, respectively, and are each measured in units of voltage.
Figure 5B:
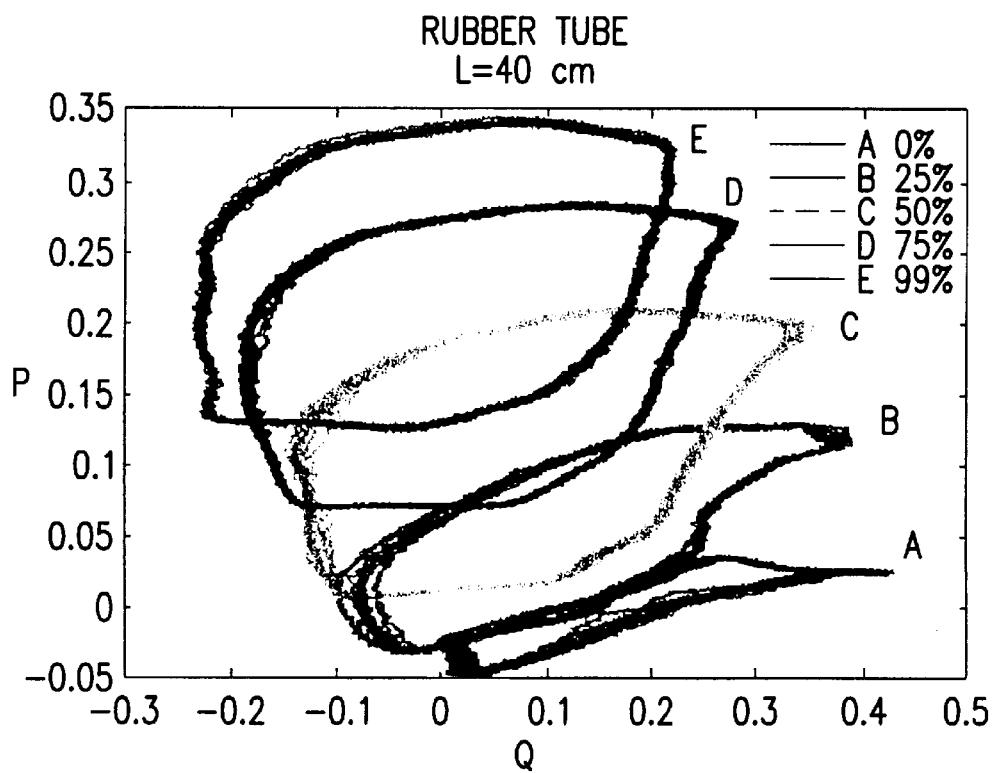
Figure 5C:
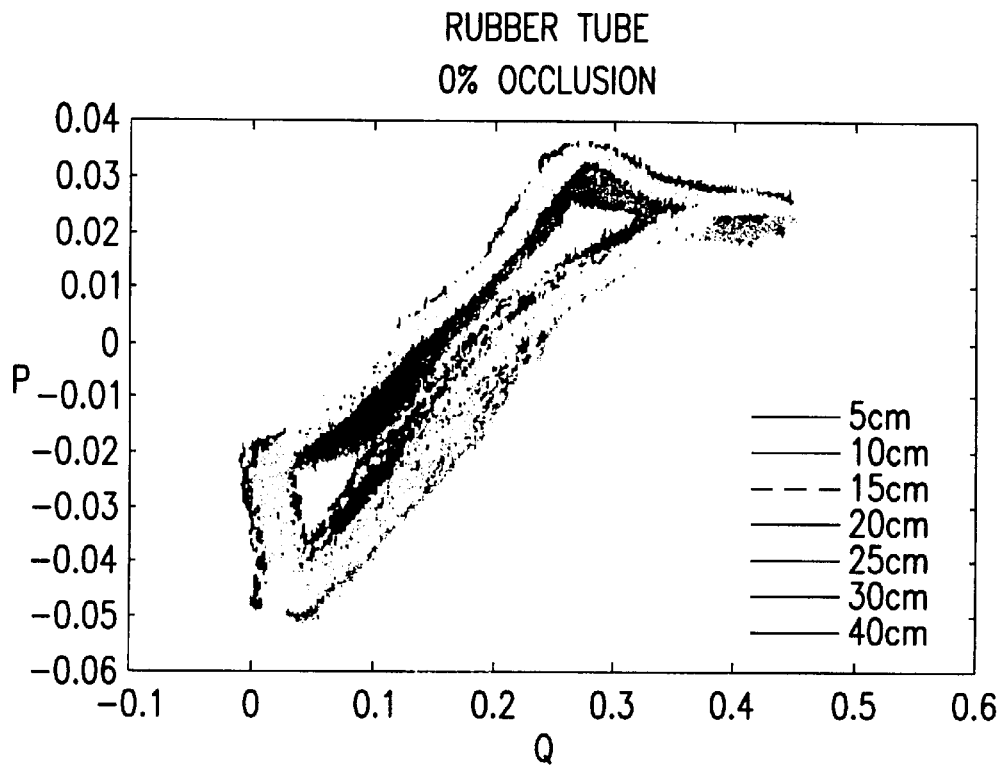
Figure 5D:
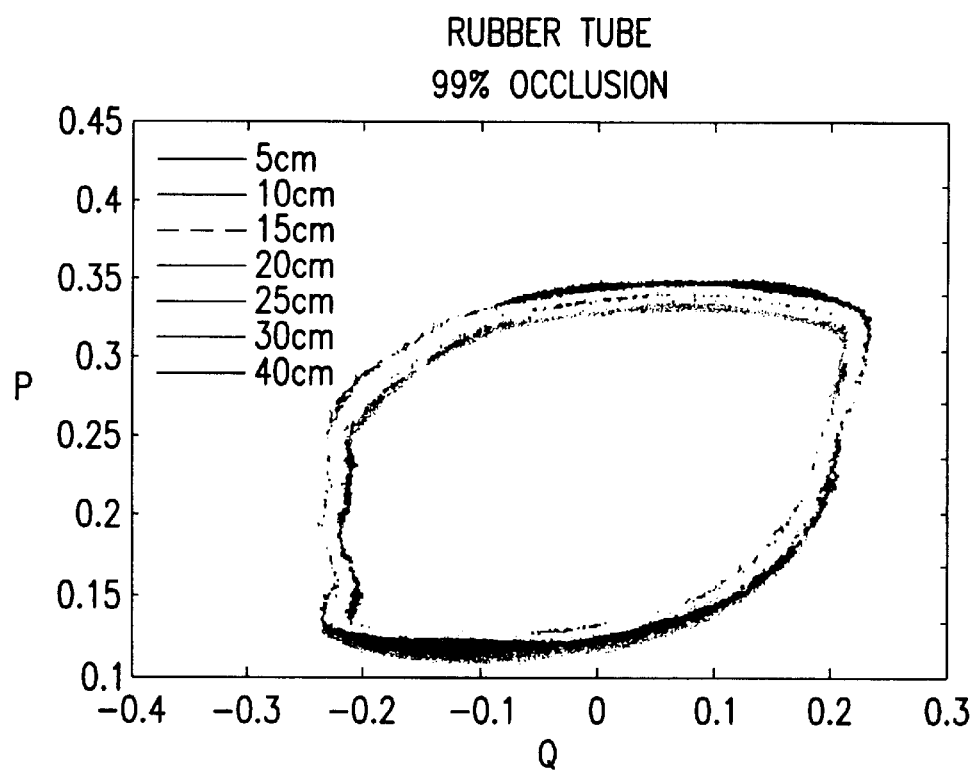
Figure 6A:
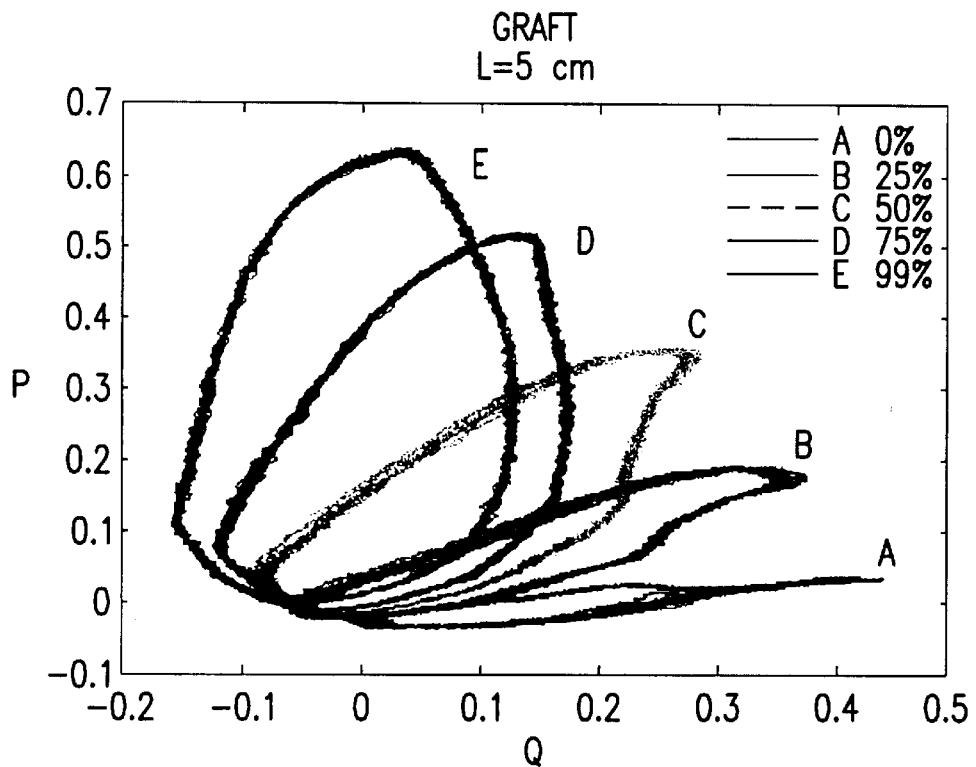
FIG. 6 is a graphical depiction of the fluid pressure-fluid flow relationship derived from in vitro measurements made in 40 cm lengths of a clinically-used vascular graft material, having external and internal diameters of 3.7 mm and 3.0 mm respectively. Fluid pressure and flow are indicated by P and Q, respectively, and are each measured in units of voltage.
Figure 6B:
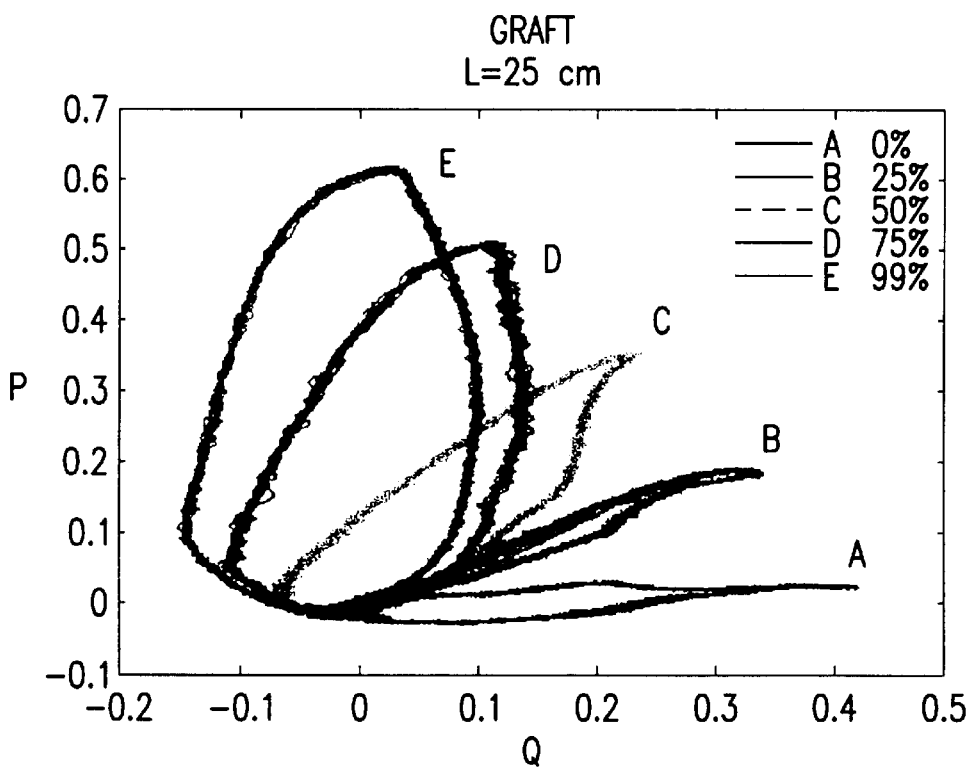
Figure 6C:
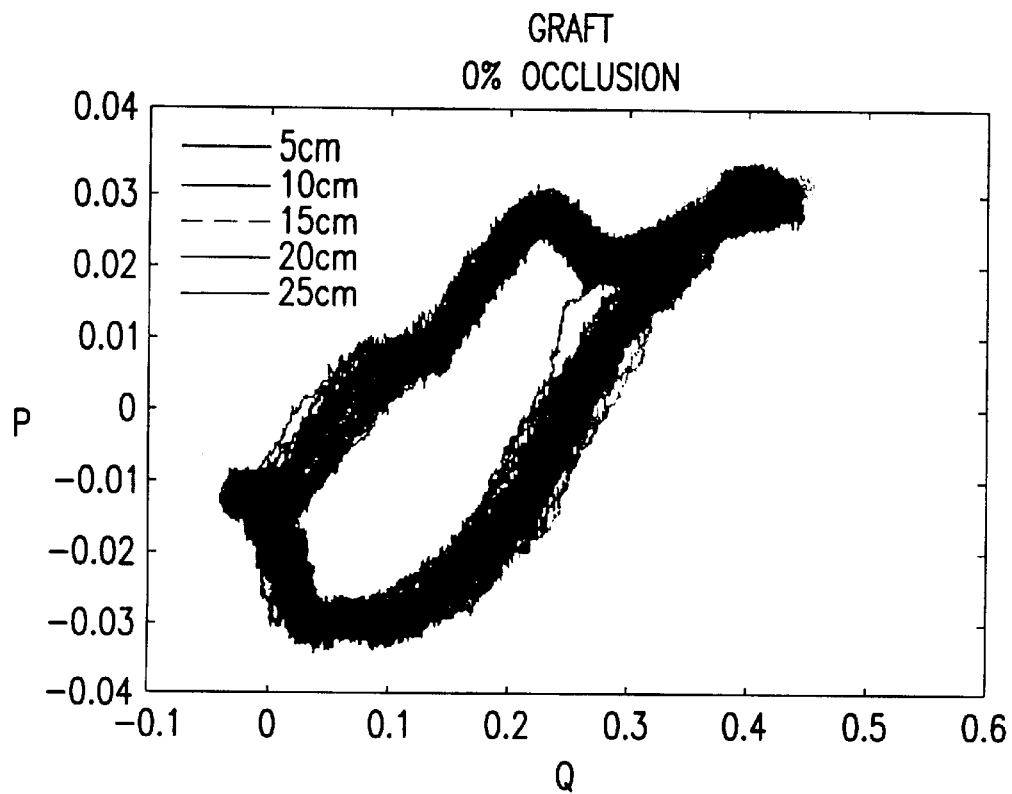
Figure 6D:
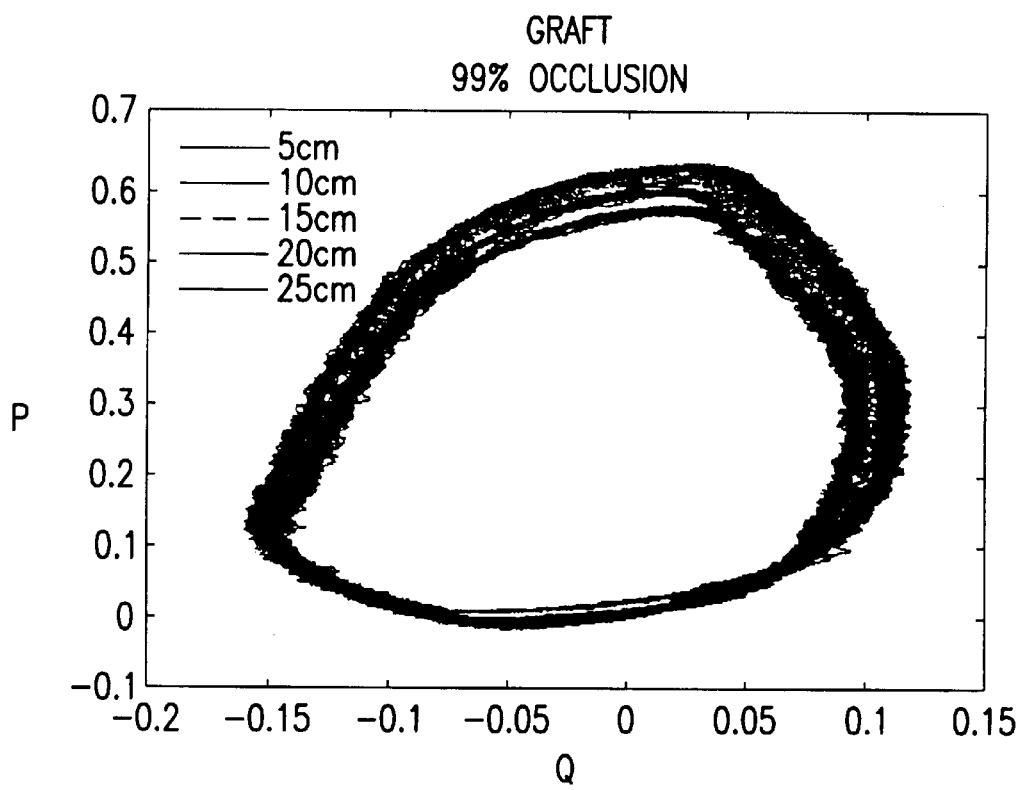

The system used (FIG. 2) consisted of an electronically controlled pulsatile pump used for producing the desired pulsating waveform. This pump is operated at a rate of 70 cycles/min, (9 volt) and is connected to a saline reservoir and to the rest of the components of the system by latex tubing having an external diameter of 5 mm and internal diameter of 3 mm.

The in vitro system was designed with parallel branches and a reservoir with saline and air (for compliance adjustment), such that the saline flow could be calibrated and controlled through the measured segment at 80 ml/min. The fluid pressure levels were set to 120 mmHg during the injection phase and 80 mmHg during the filling period. These values were chosen as they represent the mean systolic and diastolic blood pressure levels for healthy human subjects.

A Transonic flow system was used to measure fluid flow (Transonic System, Inc., Model T206, U.S.A.). The transonic flowmeter probe with 4 mm Ri (4NRB) was inserted into the tube system, proximal to the measured segment.

Controlled stenoses were induced in the measured segment using an external clamp. Millar pressure catheters of 2.5 F diameter (SPR-524, Millar Instrument, Inc., U.S.A.) were inserted into the tube system, such that the pressure measuring tip was aligned in a down-stream orientation, using a Piton™ Tri-Adaptor with a homeostatic valve (AC4002P, Medtronic, Israel) for intra-tube pressure measurement.

Results

Typical plots of fluid pressure versus time and (separately) fluid flow versus time, obtained with the above-described apparatus, using a clinically-used graft sample at 0, 25 and 50% levels of constriction, are shown in FIG. 3. The results shown in this figure indicate the changes in both flow and pressure that are seen with increasing degrees of conduit constriction.

The results of the pressure and flow measurements made in the latex tube samples are graphically depicted in FIG. 4. It may be seen from the two upper graphs that the area enclosed by the pressure-flow curve increases with increasing degrees of tube constriction, and that the same result, both qualitatively and quantitatively, is obtained whether the measurement probe is placed 5cm or 25 cm from the point of the constriction. The effect of the separation distance between the measuring probe and the site of the constriction on the pressure-flow relationship was further investigated. The lower panels of FIG. 4 depict the effect of separation distances of 5, 10, 15, 20 and 25 cm on the results obtained with both 0% and 99% occlusion. These graphs confirm that the area of the pressure-flow curve is largely independent of the distance between the measuring probe and the constriction.

Similar results were obtained with the rubber tube and with the vascular graft, and are shown in FIG. 5 and FIG. 6 respectively.

Table I summarizes the data showing the change in area enclosed by the pressure-flow curves (PFLA variable) with the degree of tubular constriction. The average and standard deviation values given are those for all three types of conduit taken together. The differences in area between the samples measured at different levels of constriction were statistically highly significant for each sample type, and also for all of the sample types taken together (p=0.00011, ANOVA).

In addition, the slope and y-axis intercept of the line joining the two inflection points situated at the extremities of the major axis of the loop-shaped pressure-flow rate graph ($\alpha$ and b in FIG. 1, respectively) were determined. Tables II and III respectively summarize the data showing the change in the slope, and y-axis intercept of the pressure-flow curves with the degree of tubular constriction. The average and standard deviation values given in these tables are those for all three types of conduit taken together. The differences in these variables between the samples measured at different levels of constriction were statistically highly significant for each sample type.

TABLE I

PFLA VARIABLE

| Degree of Occlusion | Latex tubing | Rubber tubing | Clinical graft | Average for all samples | Standard Deviation |
|---|---|---|---|---|---|
| 0% | 0.0134 | 0.0111 | 0.0142 | 0.0129 | 0.0016 |
| 25% | 0.0209 | 0.0430 | 0.0193 | 0.0277 | 0.0133 |
| 50% | 0.0596 | 0.0754 | 0.0541 | 0.0630 | 0.0110 |
| 75% | 0.1129 | 0.0859 | 0.0973 | 0.0987 | 0.0135 |
| 99% | 0.1586 | 0.0882 | 0.1333 | 0.1267 | 0.0356 |

TABLE II

SLOPE OF PRESSURE-FLOW RATE CURVE

| Degree of Occlusion | Latex tubing | Rubber tubing | Clinical graft | Average for all samples | Standard Deviation |
|---|---|---|---|---|---|
| 0% | 0.1123 | 0.1674 | 0.0886 | 0.1227 | 0.0404 |
| 25% | 0.6345 | 0.2339 | 0.4965 | 0.4550 | 0.2035 |
| 50% | 1.1258 | 0.4162 | 1.0744 | 0.8721 | 0.3957 |
| 75% | 2.1274 | 0.4684 | 2.5144 | 1.7034 | 1.0869 |
| 99% | 4.3584 | 0.4209 | 6.5998 | 3.7930 | 3.1280 |

TABLE III

Y-AXIS INTERCEPT OF PRESSURE-FLOW RATE CURVE

| Degree of Occlusion | Latex tubing | Rubber tubing | Clinical graft | Average for all samples | Standard Deviation |
|---|---|---|---|---|---|
| 0% | 0.0134 | −0.0492 | −0.0106 | −0.0155 | 0.0316 |
| 25% | 0.0189 | 0.0249 | 0.0036 | 0.0158 | 0.0110 |
| 50% | 0.0788 | 0.0457 | 0.0586 | 0.0610 | 0.0167 |
| 75% | 0.1603 | 0.1376 | 0.1449 | 0.1476 | 0.0115 |
| 99% | 0.2281 | 0.2280 | 0.3321 | 0.2628 | 0.0601 |

Figure 7A:
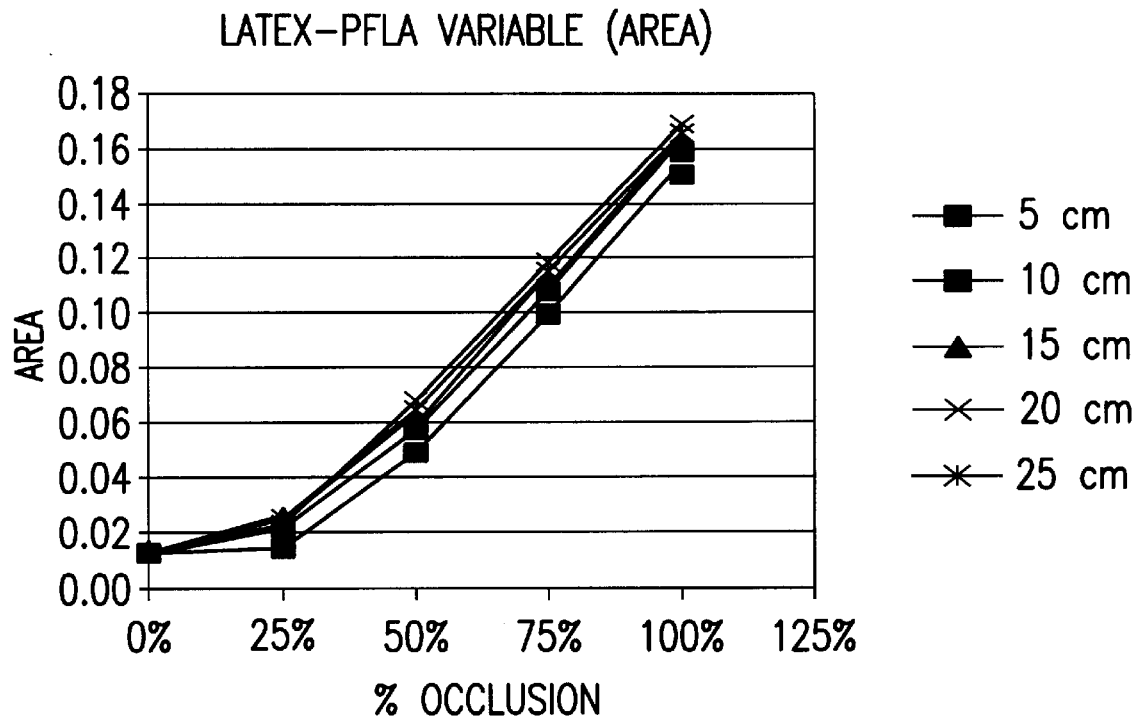
FIG. 7 graphically depicts the relationship between the area of the fluid pressure-fluid flow curve obtained with latex tubing samples and the degree of constriction. The graph on the left side gives a plot of the experimental data obtained for each of the indicated levels of constriction, while the graph on the right side shows the plot of the same data after fitting to the indicated polynomial equation.
Figure 7B:
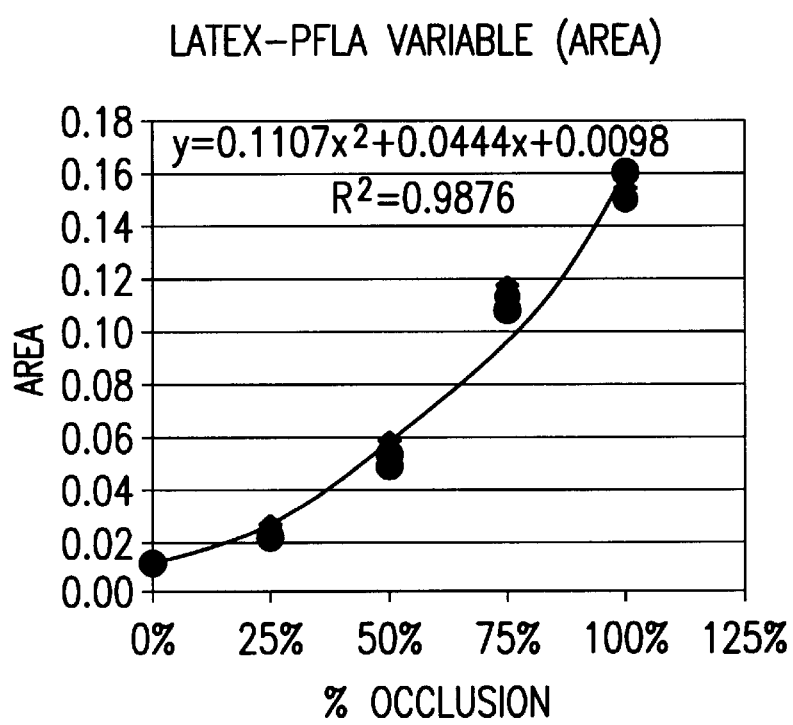
Figure 8A:
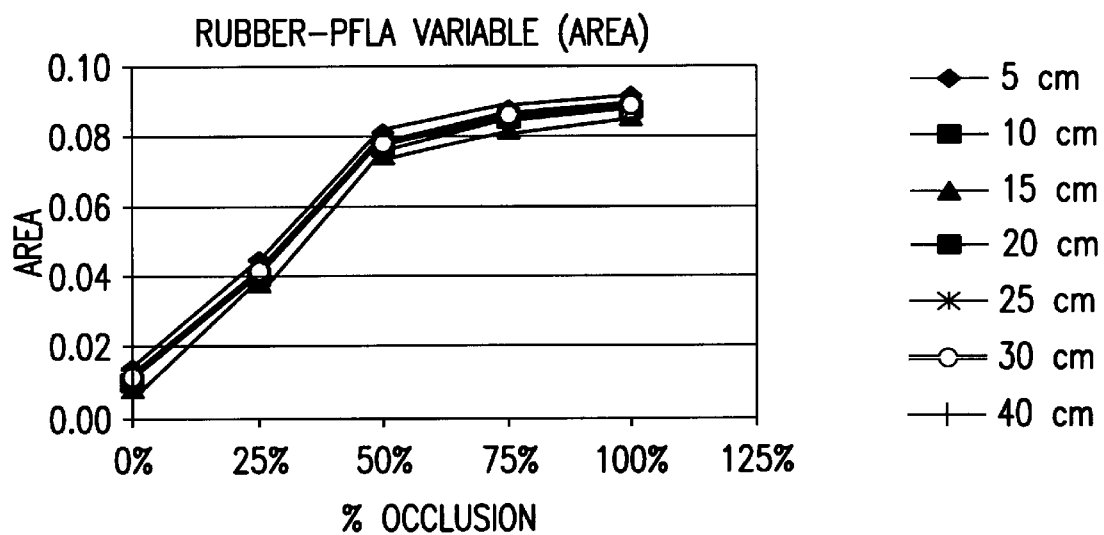
FIG. 8 graphically depicts the relationship between the area of the fluid pressure-fluid flow curve obtained with rubber tubing samples and the degree of constriction. The graph on the left side gives a plot of the experimental data obtained for each of the indicated levels of constriction, while the graph on the right side shows the plot of the same data after fitting to the indicated polynomial equation.
Figure 8B:
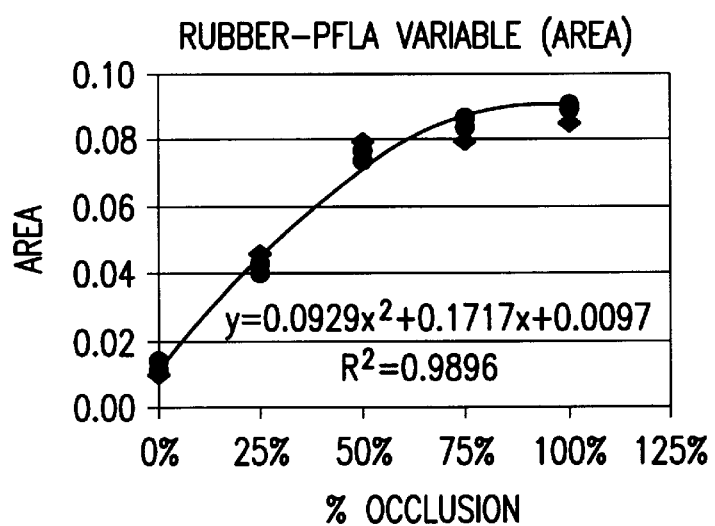
Figure 9A:
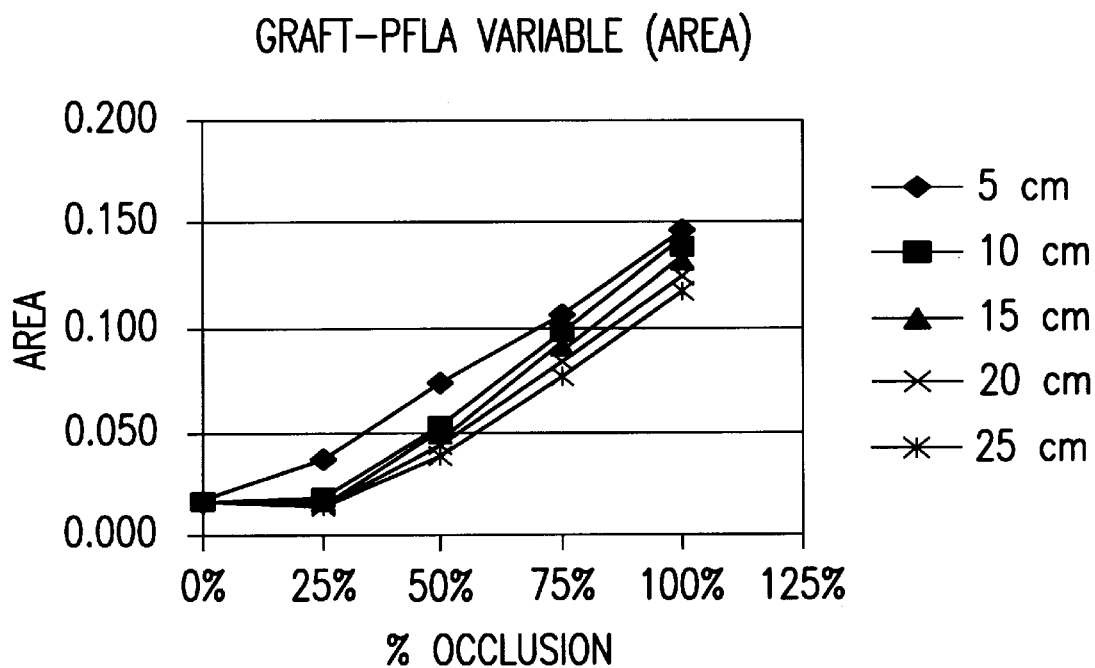
FIG. 9 graphically depicts the relationship between the area of the fluid pressure-fluid flow curve obtained with the clinical graft samples and the degree of constriction. The graph on the left side gives a plot of the experimental data obtained for each of the indicated levels of constriction, while the graph on the right side shows the plot of the same data after fitting to the indicated polynomial equation.
Figure 9B:
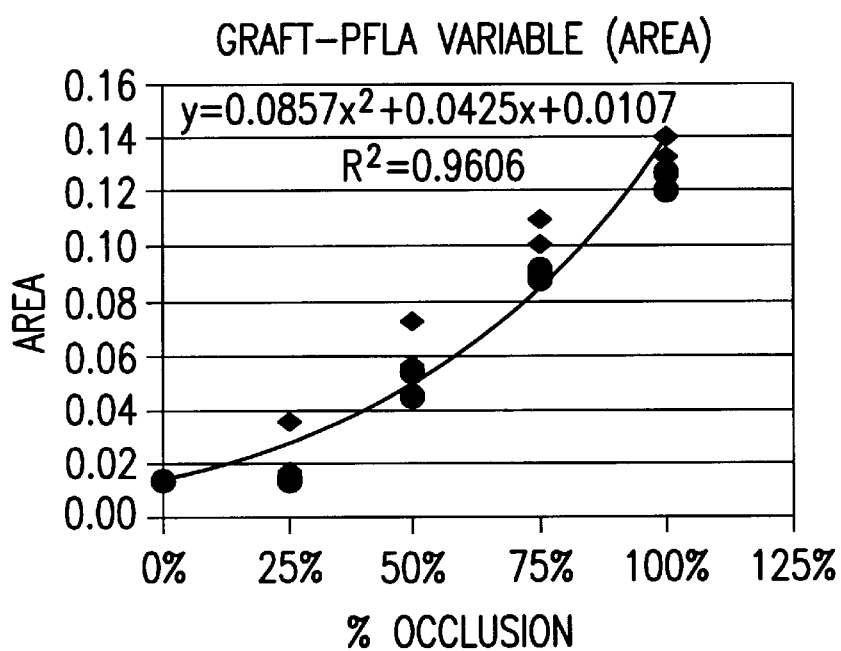

The relationship between the PFLA variable and degree of constriction is depicted graphically in FIG. 7 (latex tube), FIG. 8 (rubber tube) and FIG. 9 (graft). The plot shown on the left side of each figure is that of the data obtained experimentally, with the measuring probe located at the separation distances indicated on the graph. The plot shown on the right side of each figure shows the curve obtained after fitting the corresponding experimental data to the indicated polynomial equation.

The results presented above demonstrate that either the PFLA variable, the slope of the pressure-flow rate graph, or the y-intercept thereof, may be used to determine the degree of partial constriction of a conduit.

EXAMPLE 2

In vitro Determination of Elastic Properties of Conduits

The conduit samples and general apparatus and methods used in this study are those already described hereinabove for Example 1.

The internal fluid pressure was varied in samples of each of the conduit types, and the corresponding changes in external conduit diameter were measured using a Toolmaker's microscope (Mitutoyo, Japan). From these results, the radial compliance (Cr) for each of the conduit samples were calculated using the following relationship:

$$(dD/dD_0)/dP,$$

where $dD/dD_0$ is the change in external diameter, and $dP$ is the change in internal pressure.

Three series of measurements of compliance were made for each conduit; these values (expressed in units of 1/mmHg) are shown in Table IV. The mean values obtained for the latex tubes and for the grafts differed significantly from the result obtained for the rubber tubes ($p<0.001$). Furthermore, the value obtained for the latex tube differed significantly from that obtained for the graft ($p<0.05$).

The correlation of the mean experimentally-determined compliance values with the coefficients A, B and C of the polynomial equations describing the relationship between the degree of tubular constriction and the PFLA variable (as determined in Example 1; see FIGS. 7 to 9), was determined using correlation coefficient analysis.

The results of the correlation analysis are shown in Table V. The correlation coefficient for the correlation of the indicated polynomial coefficient (A, B or C) with the experimentally determined compliance value, is indicated in parentheses. It may be seen that there is a strong correlation between experimentally determined compliance and (taken separately) the coefficients A, B and C of the polynomial equations.

The effect of conduit elasticity on the pressure-flow curve slope and y-axis intercept ($\alpha$ and b in FIG. 1) may be seen by comparing the curves obtained for rubber conduits (FIG. 5) with conduits made of either latex or clinical graft material (FIGS. 4 and 6 respectively). Consequently, both slope and y-axis intercept may be used in place of the PFLA variable in the determination of elasticity, as outlined above.

It is thus concluded that any one of the coefficients A, B or C of the polynomial equation that describes the relationship of the PFLA variable, with the degree of occlusion of a conduit, may be used to determine the radial compliance or Young's modulus (1/compliance) of that conduit.

TABLE IV

| Tube/Series | Rubber | Latex | Graft |
| --- | --- | --- | --- |
| Series 1 | 0.00020 | 0.00015 | 0.00006 |
| Series 2 | 0.00023 | 0.00012 | 0.00003 |
| Series 3 | 0.00021 | 0.00011 | 0.00007 |
| Mean | 0.00021 | 0.00013 | 0.00005 |
| SD | 0.00002 | 0.00002 | 0.00002 |

TABLE V

| Conduit Material | Measured Compliance | A | B | C |
| --- | --- | --- | --- | --- |
| Graft | 0.0000521 | 0.0857 | 0.0425 | 0.0107 |
| Latex | 0.000128 | 0.1107 | 0.0444 | 0.0098 |
| Rubber | 0.000213 | −0.0929 | 0.1717 | 0.0097 |
| Correlation with Measured Compliance | | −0.82197 | 0.88686 | −0.89464 |

All of the above description of preferred embodiments has been provided for the purpose of illustration, and is not intended to limit the invention in any way. Many modifications can be made in the methods and apparatus of the invention. For instance, different graphical plots can be devised, and equivalent PFLA variables, and slopes and y-axis intercepts can be defined. Furthermore, many different data processing and displaying means can be used, all without exceeding the scope of the invention.

What is claimed is:

1. A method for determining the degree of partial occlusion of a conduit, comprising the steps of:
   a) producing a graphical plot of fluid pressure versus fluid flow rate through said conduit;
   b) determining the value of one or more of the following variables:
      (i) the PFLA variable consisting of the area enclosed by said graphical plot;
      (ii) the slope of the line joining the two inflection points situated at the extremities of the major axis of said graphical plot;
      (iii) the y-axis intercept of the line joining the two inflection points situated at the extremities of the major axis of said graphical plot;
   c) determining the degree of partial occlusion of said conduit by comparing one or more of the above variables, with an appropriate calibration curve, said calibration curve comprising values of the chosen variable for a conduit of the same type as the tested conduit, at predetermined known degrees of occlusion.

2. A method according to claim 1, wherein the conduit comprises a blood vessel.

3. A method according to claim 1, wherein the conduit comprises a synthetic blood vessel replacement.

4. A method according to claim 2 or 3, wherein the fluid pressure and flow rate are measured by inserting suitable probe(s) through a catheter introduced into the blood vessel or synthetic blood vessel replacement.

5. A method according to claim 2 or 3, wherein flow rate and/or fluid pressure are measured by the use of measuring devices situated external to the wall of the conduit.

6. A method according to claim 2 or 3, wherein flow rate and/or fluid pressure in the conduit are measured by the use of measuring devices situated remote from said conduit.

7. A method for determining the elastic properties of a conduit, comprising the steps of:
   a) producing a graphical plot of fluid pressure versus fluid flow rate through said conduit;
   b) determining the value of one or more of the following variables:
      (i) the PFLA variable consisting of the area enclosed by said graphical plot;
      (ii) the slope of the line joining the two inflection points situated at the extremities of the major axis of said graphical plot;
      (iii) the y-axis intercept of the line joining the two inflection points situated at the extremities of the major axis of said graphical plot;
   c) producing a graphical plot of the PFLA versus predetermined known degrees of occlusion, and deriving the polynomial equation of the plot thereby obtained, in the form of $y=AX^2+BX+C$
   d) determining the radial compliance of said conduit by separately comparing one or both of the coefficients A, B and C of the aforementioned polynomial equation with an appropriate calibration curve, said calibration curve comprising a plot of values of the chosen coefficient, A, B or C versus predetermined known levels of radial compliance; and optionally:

(1) comparing the abovementioned slope obtained with the tested conduit with the slope obtained with one or more standard conduits, to determine the relative elastic properties thereof; and/or (2) comparing the abovementioned y-axis intercept obtained with the tested conduit with the y-axis intercept obtained with one or more standard conduits, to determine the relative elastic properties thereof.

8. A method according to claim 7, wherein the conduit comprises a blood vessel.

9. A method according to claim 7, wherein the conduit comprises a synthetic blood vessel replacement.

10. A method according to claim 8 or 9, wherein the fluid pressure and flow rate are measured by inserting suitable probe(s) through a catheter introduced into the blood vessel or synthetic blood vessel replacement.

11. A method according to claim 8 or 9, wherein flow rate and/or fluid pressure are measured by the use of measuring devices situated external to the wall of the conduit.

12. A method according to claim 8 or 9, wherein flow rate and/or fluid pressure in the conduit are measured by the use of measuring devices situated remote from said conduit.

13. Apparatus for determining the degree of partial occlusion and/or the elastic properties of a conduit, comprising:

a) fluid pressure and flow rate measuring devices;

b) data receiving apparatus to receive and record data generated by said measuring devices;

c) data processing apparatus to process the data generated by said measuring devices, to determine the values of the PFLA variable, slope and y-axis intercept from the fluid pressure-flow rate curve, and to determine the degree of partial occlusion and elastic properties therefrom;

d) algorithms, associated with said apparatus, for performing the data processing tasks.

14. Apparatus according to claim 13, further comprising a visual display apparatus.

15. Apparatus according to claim 13, or 14, further comprising means for producing a printed output.

* * * * *